United States Patent [19]

Zoltán et al.

[11] Patent Number: 5,153,349
[45] Date of Patent: Oct. 6, 1992

[54] PROCESS FOR THE PREPARATION OF CYPERMETHRINE ISOMERS

[75] Inventors: Sándor Zoltán; György Hidasi; Béla Bertók, all of Budapest; Istaván Székely, Dinakeszi; Janis Hajimichael; Sándor Botár, both of Budapest; Lajos Nagy, Szentendre; Éva Somfai; István Lak, both of Budapest; András Rapi, Erd; Antal Gajáry, Budapest; Ágnes Hegedüs, Budapest; Mária Tary, Budapest, all of Hungary

[73] Assignee: Chinoin Gyogyszer- es Vegyeszeti Termekek Gyara Rt., Budapest, Hungary

[21] Appl. No.: 601,767

[22] PCT Filed: Jan. 17, 1990

[86] PCT No.: PCT/HU90/00006

§ 371 Date: Oct. 19, 1990

§ 102(e) Date: Oct. 19, 1990

[87] PCT Pub. No.: WO90/08132

PCT Pub. Date: Jul. 26, 1990

[30] Foreign Application Priority Data

Jan. 17, 1989 [HU] Hungary ............................. 167/89
Dec. 27, 1989 [HU] Hungary ............................. 6780/89

[51] Int. Cl.⁵ ................. C07C 253/32; C07C 253/34; C07C 255/32
[52] U.S. Cl. .................................... 558/354; 558/355; 558/407
[58] Field of Search .................. 558/407, 355, 354

[56] References Cited

U.S. PATENT DOCUMENTS

| | | | |
|---|---|---|---|
| 4,308,279 | 12/1981 | Smeltz | 424/304 |
| 4,512,931 | 4/1985 | Robson | 260/465 D |
| 4,681,969 | 7/1987 | Williams et al. | 514/521 X |
| 4,845,126 | 7/1989 | Hidasi et al. | 514/521 |
| 4,997,970 | 3/1991 | Ager, Jr. | 558/354 |

FOREIGN PATENT DOCUMENTS

WO86/04215 7/1986 PCT Int'l Appl.
WO88/10249 12/1988 PCT Int'l Appl.
2064528A 1/1981 United Kingdom.

*Primary Examiner*—Joseph Paul Brust
*Attorney, Agent, or Firm*—Herbert Dubno; Jonathan Myers

[57] ABSTRACT

The invention relates to a process for the preparation of such isomer mixtures of cypermethrine of the Formula (I)

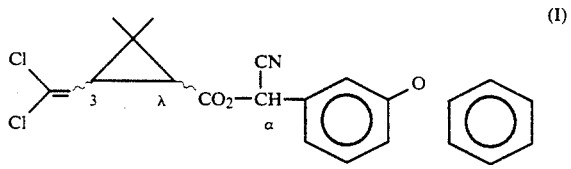

wherein carbon atoms indicated by 1, 3 and α stand for a chiral carbon atom and the wavy line indicates cis or trans configuration related to the cyclopropane ring— which contains out of the theoretically possible 8-isomers of cypermethrine at least 95% of 1RtransS and 1StransR (Ib) isomer pair or only a mixture of 1RcisC and 1ScisR (Ia) and the isomer pair (Ib) of the ratio (Ia):(Ib)=55:45-25:75 by asymmetric transformation of second order performed in the presence of an amine base and solvent from a starting cypermethrine isomer mixture which contains next to the isomer pair (Ib) cis and other trans isomers or the isomer pair Ia+Ib at an undesired ratio.

11 Claims, No Drawings

PROCESS FOR THE PREPARATION OF CYPERMETHRINE ISOMERS

The present invention is directed to the preparation of enantiomer mixtures of α-cyano-3-phenoxybenzyl-3-(2,2-dichlorovinyl)-2,2-dimethyl-cyclopropane-carboxylate (referred to hereinafter as cypermethrin of the formula (I)

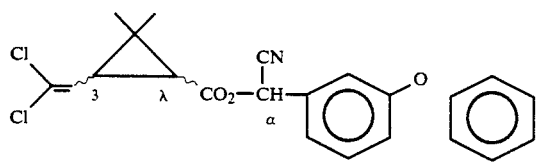

of given isomer ratio by asymmetric transformation.

In the disclosure the steric configuration of the substituents related to the chiral carbon atom (indicated as α in the formula) is characterized by the symbols S and R. The terms "cis" and "trans" are used to indicate the position of the substituents on the $3^{rd}$ carbon atom of the cyclopropane ring, and the absolute steric configuration of the substituent of the $1^{st}$ carbon atom is given as premember 1R and 1S. The following abbreviations are used to indicate the various enantiomers and enantiomer pairs:

Ia: mixture of 1RcisS and 1ScisR; alphamethrin (Fastac)
Ib: mixture of 1RtransS and 1StransR (Transmix)
Ic: mixture of 1RcisR and 1ScisS
Id: mixture of 1RtransR and 1StransS
If: 1RcisS
Ig: 1RtransS
Ih: 1ScisR
Ii: 1StransR
Ia+Ib: asymmethrin (Chinmix).

The present invention is directed to such isomer mixtures of cypermethrine of the formula (I)

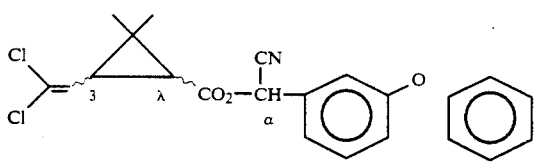

which contains out of the theoretically possible 8 isomers of cypermethrin at least 95% of 1RtransS and 1StransR (Ib) isomer pair or only the mixture of 1RcisS and 1ScisR (Ia) and (Ib) isomer pairs at a ratio of (Ia):(Ib)=55:45-25:75 by an asymmetric transformation of II. order in the presence of an amine base and a solvent starting from a cypermethrin isomer mixture containing in addition to the (Ib) isomer pair cis and other trans isomers or the isomer pair of (Ia)+(Ib) at an undesired ratio and the process is carried out by a) reacting an oily or crystalline isomer mixture of the Formula (I) of at least 90% by weight purity containing at least 60% of trans isomers or cis:trans isomers at a ratio of 65:35-15:85 at a temperature of 0°-25° C. in a system containing up to 0.5% moisture with 0.1-0.5 parts by weight of triethyl amine or 0.0005-0.01 parts by weight of 1,5-diazabicyclo[4.3.0]non-5-ene (DBN) or 1,5-diazabicyclo[5.4.0]undecene (DBU) related to the weight of the starting isomer mixture under intensive stirring, in the presence of propanol at the saturation point of the isomer mixture of the desired ratio while adding to the mixture simultaneously with the epimerization reaction propanol and optionally triethyl-amine so that the ratio of propanol related to cypermethrin is at the end of the reaction 0.5-2 parts by weight and while under optional gradual cooling a crystalline product precipitates, and b) after completing the asymmetric transformation the isolated crystalline mass is treated with an aqueous acid solution and/or dissolved in the presence of an organic water-inmiscible solvent at 0°-70° C. or melted without any solvent at 60°-70° C. and washed with an aqueous acid solution and the organic layer is washed with water optionally containing salts or acids and/or the raw product is recrystallized from a solvent containing organic acid and c) as a cyan binding agent an aldehyde is added to the working up section of the operation sequence, whereas optionally d) the sequence of operations is continuously carried out in several reactors by forming a reactor chain by connecting into series 2-10 reactors, which can be cooled and heated and contains a mixer and the elements next to each other are adjusted within a temperature range of (+)30°-(−)25° C. to at most 10° C. temperature difference, and at the beginning 1 part by weight of a desired end product crystal and optionally up to 0.4 parts by weight base are added to each reactor element and the mixtures in each reactor are optionally diluted with an additional 0.4 parts by weight of protic solvent whereafter to the first reactor 1 part by weight of raw isomer mixture of the formula (I) of at least 90% purity and optionally a further amount of base is added to result in 0.4 parts by weight, and optionally up to 0.4 parts by weight of protic solvent is added, the mixture is stirred and the reaction mixture or a part thereof is introduced to the second and subsequent reactors where the addition of the protic solvent and base and the stirring is optionally repeated several times, while the raw cypermethrin is repeatedly added continuously or discontinuously to the first reactor together with up to 0.4 parts by weight of protic solvent and/or a base while the reaction mixture passes in order through all reactors under the above treatment, and the crystals are optionally isolated from the obtained crystal suspension at the end of the reactor chain.

The above isomers of cypermethrin are insecticides with favorable biological properties (EP 205.010 and EP 208.758).

During the known processes the desired isomer mixture is separated by crystallization starting from cypermethrin isomer mixture.

The crystallization is carried out in the presence of a base which is suitable to induce epimerization on the α-carbon atom, and the undesired isomers can theoretically be transformed to desired product. This process is known in the organic chemistry as "an asymmetric transformation of II. order".

According to processes disclosed for purely cis isomers the (Ia) isomer is prepared from the mixture of cis cypermethrins. The starting material was suspended in a 1.5-3.0-fold excess of triethyl-amine or it was dissolved hot and seeded with a crystal of (Ia) containing 1RcisS and 1ScisR isomers at a ratio of 1:1 and the solution or suspension was crystallized slowly by gradual cooling.

Ia of a purity of 90-95% was obtained with a yield of about 80% (EP 67461 and 109113).

Similar processes were published for the preparation of Ib starting from cypermethrin containing Ib+Id trans isomers by epimerization with an organic or inorganic base, or by epimerization in the optional presence of an organic solvent, such as petrol ether and 2,6-di-tert-butyl-4-methyl-phenol as antioxidant at 30°-60° C. (EPA 215.010).

According to a further publication Ia, Ib and Ia+Ib were prepared by contacting a hydrocarbon slurry of the starting isomers with a base and a catalyst, the catalyst being substantially soluble in the slurry and selected from a quaternary ammonium compound, a quaternary phosphonium compound and a crown ether, agitating the slurry while maintaining a temperature effective for conversion, and recovering the resulting isomers. The tendency to form benzoine ester by-products was reduced by including in the slurry an aldehyde scavenger such as a metabisulfite, and/or a tetraalkyl-ammonium halide catalyst dissolved in an aprotic solvent such as an organic nitrile. Inorganic bases were used in solid form or as aqueous solutions. The preferred base is said to be sodium cyanide (PCT Publication WO 88/10249).

The disadvantage of this process is a significant decomposition under the suggested reaction conditions accompanied e.g. by the formation of benzoine derivatives of the Formula (II)

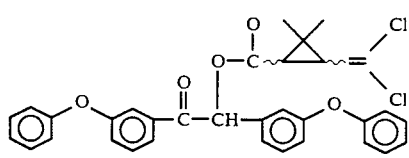
(II)

The suggested "scavenger-molecule" prevents only the formation of the benzoine derivatives but not the decomposition of cypermethrin. As a further disadvantage the release of cyanide can be mentioned during the working up as a by-product of the decomposition. The treatment of the reaction mixture consisting of several layers further complicates the reliable industrial realization of this critical reaction. May be that is why in the numerous examples of this publication no yield results are reported. The increased difficulties occurring with the mixtures containing together isomers Ia and Ib are shown by EP 67461 as well, where the preparation of the isomer pair of Ia is disclosed by transforming (Ia+Ic) isomer mixture in triethyl amine. According to this publication the presence of 6 or 10% trans isomer contamination in the starting material reduced the yield of Ia to 63 or 36%. In case of a higher trans isomer content the crystallization of Ia could not be expected and even less the isolation of mixture (Ia+Ib).

According to a known process pure Ia+Ib can be prepared by selective crystallization of cypermethrine of sufficient purity by choosing suitable conditions, like solvent, temperature and pure seeding crystal. The process lasts several weeks. Thus, the Ia+Ib mixture can be obtained with a yield of 80% calculated to the Ia+Ib isomer pair content of the starting cypermethrin. The disadvantage of the process is that the other biologically less valuable stereoisomers of cypermethrin remain unutilized (EP 208.758).

The industrial preparation of isomer pure products (active ingredient content above 97%) is still problematic. Particularly, the mixtures containing Ia show a skin-irritating effect inducing in individuals serious allergy and therefore the simplification of the working up was intended.

The epimerization according to the present invention is to be conducted in a system containing up to 0.5% moisture. According to our results a catalytic amount of water can already influence the formation of benzoine derivatives of the Formula (II). As opposed to previous processes we do not bind the decomposition products but prevent the hydrolytic decomposition of cypermethrin.

According to the invention an industrial process can be performed by combining the elements a), b) and c) and optionally d) and this process results in stable pure products which can be obtained with a good yield and simple, safe process, which is acceptable from health protecting point of view as well.

The elements are further detailed as follows:

The element a) of the process of the invention is based on the recognition that from the point of view of a successful asymmetric transformation of second order not only the selection of a suitable base is critical for maintaining the rate of the matched epimerization and crystallization process but also a given amount of propanol has to be added simultaneously with the epimerization reaction at a suitable temperature. It was observed that if to the oily cypermethrin isomer mixture a solvent suitable for crystallization, such as isopropanol is added, then the solvent is dissolved to a certain extent by cypermethrin and then at a so-called saturation or equilibrium value the mixture suddenly turns to an emulsion. By further addition of the solvent the formed emulsion gradually turns to a real solution. The same phenomenon can be observed if the solvent suitable for crystallization contains a base as well. According to our observation the asymmetric transformation can be carried out most quickly at the saturation or equilibrium value. As to our knowledge this observation has not yet been published in connection with asymmetric transformation. The rate of transformation is reduced by the progression of the product formation but it may be improved by adding further propanol (propanol selectively promotes the crystallization of Ia and Ib). This process is further promoted by cooling the mixture.

This equilibrium or saturation condition, however, means a narrow interval and consequently the composition of the formed product is already influenced by a small deviation. If the temperature is raised from 14°-15° C. to 20° C. when preparing an isomer mixture of Ia:Ib=4:6, then a significant yield reduction and an enrichment of the Ib enantiomer pair can be observed instead of the thermodynamically expected Ia enantiomer pair of the higher melting point (86° C.). The same can be achieved by deliberately increasing the amount of the solvent. The process of the invention makes it possible to get a product diferring from the cis:trans composition of the starting cypermethrin even by 30% by weight and a product can be isolated which has the desired isomer ratio. As a starting material both oily and crystalline cypermethrin isomer mixtures can be used. When using a crystalline starting material, the epimerization reaction can be realized more quickly, even if the reaction is performed discontinuously.

The preparation of some important Ia:Ib isomer pairs is detailed as follows.

In order to prepare mixtures wherein the isomer ratio Ia:Ib=40:60 as a starting material a cypermethrin mixture is used of the isomer ratio (Ia+Ic)=35-45, (Ib+Id)=50-60% by weight, and the reaction is continued for 4-10 days depending on the amount at 3°-16° C., then for 1-5 days at 0° C. while the ratio of cypermethrin:triethyl-amine:propanol is 1:0.2-0.3:1-1.5. The addition of propanol is preferably started from the second day and continued until the 5th day.

If a mixture of Ia: Ib=50:50% by weight is prepared then an isomer mixture of (Ia+Ic)=40-55, (Ib+Id)=45-55% by weight is used as starting material and the isomerization is continued for 1-10 days.

If an isomer mixture of Ia:Ib=25-30:75-70% by weight is to be prepared then an isomer mixture of Ia+Ic=35-45=(Ib+Id)=50-60% by weight is used as starting material. The asymmetric transformation and the isolation is carried out for 1-5 days at 25° C.

It is preferred to cool the reaction mixture below 0° C. and precrystallize if an oily cypermethrin is used as starting material.

The small amount of (Ic+Id) isomer pairs being present in the isolated product due to the washing of the filtered crystalline end-product can be further reduced. As washing solvents hexane, heptane, petrol ether, ethanol and/or isopropanol or mixtures of these solvents with acids, such as acetic acid, phthalic acid, maleic acid, fumaric acid and malonic acid or alkylated malonic acid can be used.

The asymmetric transformation can be performed in the presence of both isopropanol and n-propanol.

It is an important feature of our process that in the last third term of the reaction time the reaction mixture is gradually cooled below 0° C., preferably below $-10°-(-25)°$ C.

We have found that a small amount of basic, such as nitrogen containing contamination, results in the epimerization of the end-product. The same epimerization can be caused by contamination in the introduced solvent or by any of the residual reactants during the preparation or by contaminations introduced with added materials during the formulation. In the tables attached to the examples it is shown how the undesired epimerization can be prevented by suitably added acids (represented by the introduction of a small amount of triethyl amine) and how the products can be stabilized. The investigations led to the element b) of our process.

According to element b) of the present invention the reaction mixture can be acidified or the crystalline suspension can be digested by using 0.1-5% by weight of aqueous acid, preferably hydrochloric acid, formic acid, phthalic acid, malonic acid, fumaric acid or alkylated malonic acid or maleic acid, optionally containing a cyano binding agent.

For the extraction of the crystalline suspension a water inmiscible organic solvent, preferably hexane, cyclohexane, petrol ether, dichlormethane, dichlorethane, chloroform, carbon tetrachloride, ethylacetate, benzene, toluene or xylene may be used. It is preferred if the extract is washed with water or with water saturated with sodium chloride and/or with a 0.1% by weight of aqueous mineral or organic acid, preferably hydrochloric acid, acetic acid, phthalic acid, malonic acid, alkylated malonic acid, fumaric acid or maleic acid solution.

In order to recrystallize the product an apolar or protic solvent, preferably hexane, heptane, petrol ether, methanol, ethanol, isopropanol or a mixture thereof with acid, preferably acetic acid, maleic acid, fumaric acid, malonic acid or alkylated malonic acid can be used.

The product is always obtained as a crystal, a melt or a solution at the end of the sequence of operations. The product shows a stable isomer ratio after 12 months as well.

If the reaction is carried out under anhydrous conditions, then as mentioned above the decomposition of cypermethrin can be prevented. The supression of the decomposition also reduces the cyanide content of the reaction mixture.

During the long treatment, however, a small decomposition can occur in the reaction mixture under industrial conditions. Therefore according to element c) of our invention we also ensured that no problem should be caused by the appearance of the free cyanide from the point of view of safety. At each time when it would be possible that a small amount of free cyanide appears by the acidification of the medium an aldehyde is added to the reaction mixture as a stable cyanide binding agent to prevent cyanide getting into the air space. Preferably formaldehyde is used. The so obtained cyano glycolic acid nitrile in the waste mixture can be hydrolyzed also to glycolic acid by simple heating and the so obtained mixture can be processed without danger.

The asymmetric transformation of II. order is a heterogeneous equilibrium reaction consisting of two steps. The determination of the reaction kinetics of such reaction is only possible by experiment. In our case the process is made more complicated as the concentration changing with the progression of crystallization is further diluted and the epimerization reaction temperature can be raised and then decreased by the progress of the process. In order to clarify if the reaction kinetics of the process makes the use of a cascade reactor theoretically possible the order of the reaction was determined. The reaction can be described with an apparent kinetics of second order, and this means that the use of a continuous or quasi continuous reactor chain can increase the capacity and the conversion which can be achieved within time unit, respectively.

The element d) of our invention is based on the recognition that on the basis of the reaction kinetics of the asymmetric transformation of second order of cypermethrin the process can be performed more favorably by using a continuous or quasi continuous cascade reactor. The reaction can be performed continuously or quasi continuously. In the first case the materials are charged or discharged continuously whereas in the second case the material is charged by portion so that the reactor chain functions without interruption. Several reactor chains can be formed parallely with each other. It is preferred to use trans connections in the reactor chain thus recirculation or bypass can be carried out. The advantage of the method is that the capacity can be multiplied related to several batch reactors and the conversion of the transformation can be improved as well. The formed product can be processed continuously and therefore the decomposition or aggregation due to standing can be avoided. The desired conversion can be achieved during a shorter time related to material unit and thus the danger of decomposition can be reduced. The apparatus can be maintained at constant temperature saving thereby energy.

The present invention also provides stable arthropodicidal compositions containing as active ingredient an isomer mixture of cypermethrin of the formula (I) which contains at least 95% by weight of an enantiomer pair of 1RcisS and 1ScisR (Ia) and an enantiomer pair of 1RtransS and 1StransR (Ib) at a ratio of Ia:Ib=55:45-25:75 or the isomer pair Ia or Ib and as a stabilizer the composition contains 0.001-0.1% by weight related to the active ingredient of an acid or acid mixture, preferably non-volatile carboxylic acids of $pK_1$=1-5 such as phthalic acid, succinic acid, tartaric acid, maleic acid, fumaric acid, malonic acid or once or several times substituted alkylated derivatives thereof and/or oxalic acid.

When carrying out the process d.) according to our invention using continuous or intermittent feed it is preferable to use the following concentrations in the starting reaction mixture: 50-80 w % of cypermethrine, 1-50 w % of propanol, 10-20 w % of triethyl amine or 0.0002-0.01 w % of DBN or DBU.

It is also advantageous to assure that the concentrations in the final reaction mixture after accomplishing asymmetrical transformation should be the following: 25-45% of cypermethrin, 45-75 w % of propanol, 4-14 w % of triethyl amine or 0.0002 w %-0.004 w % of DBN or DBU.

In a continuous process the velocity of flow of the reaction mixture should be 50-150 g/hour/liter of useful volume of the reactor system.

The stabilized solutions or products, containing the cypermethrin isomers as defined above along with the stabilizing acids mentioned above may be used in admixture with additives used in pesticide industry for agricultural, veterinary, human health and/or hygienical purposes (see e.g. EP 208,758). The use of additives that might counteract the stabilizing action of the acids, especially the use of bases has to be avoided or has to be taken in account when defining the quantity of acid used. Also the solvents have to be chosen accordingly.

The further details of our invention are illustrated in the following examples.

The used and isolated substances were analyzed by HPLC technique. See Analythical Methods for Pesticides and Plant Growth Regulators: XIII, Ed. by G. Zweig and J. Sherma, Academic Press, 1984.)

Where it is not specially mentioned the water content of the reactants is below 0.1% by weight.

EXAMPLE 1

Preparation of a 40:60 mixture of 1RcisS and 1ScisR enantiomer pair Ia and 1RtransS and 1StransR enantiomer pair Ib from cypermethrin To an apparatus equipped with a magnetic stirrer 100 g crystalline cypermethrin of 99% by weight purity (m.p.: 38°-43° C., isomer ratio: Ia=18.1% by weight, Ib=23.1% by weight, Ic=23.5% by weight, Id=34.3% by weight) are suspended in a mixture of 21.7 g triethyl-amine and 23.5 g isopropanol, and the mixture is stirred for 24 hours at 16° C. The gradually thickening suspension is diluted four times with 31.5 g isopropanol each in every 24 hours and then the mixture is further stirred for 24 hours at 0° C. The thick suspension is filtered, washed with 39.3 g isopropanol, 31.5 g isopropanol containing 0.25% by weight of acetic acid and with 23.5 g further isopropanol and dried in vacuo at room temperature. 87 g snow-white crystalline substance are obtained.

M.p. 62°-63° C.

Isomer ratio: Ia=38.0% by weight, Ib=59.3% by weight, Ic=1.2% by weight, Id=0.4% by weight.

Purity: 98.9% by weight.

The mother lye is evaporated and the process described above is repeated with the obtained 13.5 g of product and with a mixture of 13.0 g isopropanol and 2.8 g triethyl-amine and as a second generation further 7 g of snow-white crystalline substance are obtained.

M.p.: 62°-65° C.

Isomer composition: Ia=48% by weight, Ib=48.2% by weight, Ic=1% by weight, Id=0.4% by weight.

Purity: 97.6% by weight.

EXAMPLE 2

Preparation of a 40:60 mixture of 1RcisS and 1ScisR (Ia) and 1RtransS and 1StransR (Ib) from cypermethrin One may proceed as given in Example 1 but the crystalline cypermethrin is replaced by 100 g thick oily cypermethrin (purity: 95.6% by weight, isomer composition: Ia: 17.6% by weight, Ib: 22.6% by weight, Ic: 22.9% by weight, Id: 32.4% by weight) are used and the reaction is performed at 11° C. By combining generations I and II 91 g (91%) of snow-white crystalline product are obtained.

Mp.: 62°-64° C.

Isomer composition: Ia: 38.1% by weight, Ib: 58.1% by weight, Ic: 1.1% by weight, Id: 0.7% by weight.

Purity: 98% by weight.

EXAMPLE 3

Preparation of a 50:50 mixture of 1RcisS and 1ScisR (Ia) and 1RtransS and 1StransR (Ib) from cypermethrin One may proceed as given in Example 1 but as starting material 100 g crystalline cypermethrin are used (purity: 98% by weight, Ia: 22.3% by weight, Ib: 20.4% by weight, Ic: 26.6% by weight, Id: 28.7% by weight). From the combined generations I and II 95 g snow-white crystalline product are obtained.

Mp.: 64.5°-65.5° C.

Isomer composition: Ia: 48.2% by weight; Ib: 48.4% by weight; Ic: 1.1% by weight; Id: 0.6% by weight.

Purity: 98.3% by weight.

EXAMPLE 4

Preparation of 1RcisS and 1ScisR (Ia) and 1RtransS and 1StransR (Ib) from cypermethrin at 25° C.

The starting material is the same as given in Example 1, but epimerization is carried out at 25° C., and 52.1 g crystalline snow-white product is obtained.

M.p.: 65°-68° C.

Isomer composition: Ia: 28.8% by weight; Ib: 67.3% by weight; Ic: 0.8% by weight; Id: 0.3% by weight.

Purity: 97.2% by weight.

EXAMPLE 5

Preparation of 1RcisS and 1ScisR (Ia) and 1RtransS and 1StransR (Ib) from cypermethrin with DBN The starting mixture is the same as used in Example 1 but triethyl-amine is replaced by 0.1 g DBN and from the generations I and II 95 g white crystalline product are obtained.

M.p.: 62°-64° C.

Isomer composition: Ia: 39.4% by weight; Ib: 57.4% by weight; Ic: 1.2% by weight; Id: 0.8% by weight.

Purity: 98.8% by weight.

EXAMPLE 6

Preparation of 1RcisS and 1ScisR (Ia) and 1RtransS and 1StransR (Ib) of a ratio of 40:60 from cypermethrin with n-propanol To an apparatus equipped with a magnetic stirrer, thermometer and having 2 openings 100 g of cypermethrin oil are added (purity 91.4% by weight, Ia: 16.6% by weight, Ib: 21.5% by weight, Ic: 21.8% by weight, Id: 31.5% by weight). The material is stirred in the mixture of 14.5 g of triethyl-amine and 24.1 g n-propanol for 4 days at 10°–12° C. In the mean time the suspension is diluted after 24 hours with a mixture of 14.5 g triethyl-amine and 16 g n-propanol and the dilution is repeated in every 24 hours with 24.1 g n-propanol 3 times. After the addition of the last solvent portion the temperature of the reaction mixture is cooled to 5° C. and it is stirred for another 24 hours.

The precipitated crystals are filtered and washed contamination-free as described in Example 1 and the product is dried. In the first generation 82 g of snow-white crystalline substance is obtained.

M.p.: 62°–63° C.

Isomer composition: Ia: 38.0% by weight; Ib: 60.0% by weight; Ic: 1.0% by weight; Id: 0.5% by weight.

Purity: 99.5% by weight.

After evaporating the mother liquid is recrystallized as given in example 1.

EXAMPLE 7

To a duplicator equipped with controlled cooling and vapour heating and propeller stirrer of 3000 liter capacity 600 kg of cypermethrin oil (purity: 92% by weight, composition: (Ia+Ic)=42% by weight, (Ib+Id)=50% by weight), 180 kg of anhydrous isopropanol (water content: max. 0.2% by weight) 180 kg of anhydrous triethyl-amine (water content: max. 0.2% by weight) are added and the mixture is dissolved under stirring. Optionally 4 kg of (Ia=38% by weight, Ib=58% by weight) cypermethrin seeding crystals can be added for seeding at 25° C. In order to carry out the asymmetric transformation the solution is stirred at 3°–7° C. for 18 hours, and to the crystallizing mixture 228 kg anhydrous isopropanol are added. The mixture is stirred again for 24 hours at 3°–7° C., 96 kg anhydrous isopropanol are added, the mixture is stirred for 24 hours at 3°–7° C. and finally 96 kg of anhydrous isopropanol are added by suction and the mixture is further stirred for 168 hours at 3°–7° C.

The reaction mixture is then cooled to 0°–(−5)° C. and stirred for 96 hours. The obtained crystal-suspension is filtered on a pressure filter in 4 equal portions with nitrogen. The 120 kg crystalline mass is washed as a filter cake with anhydrous isopropanol, filtered, elutriated with 4% by weight of acetic acid-isopropanol solution and filtered with nitrogen pressure. The obtained crystals are dried for 12 hours at 40°–45° C. under heating and stirring in a vacuo dryer equipped with a band stirrer. 500 kg of asymmethrin are obtained. Its composition according to GC analyzis: (Ia)=38.2% by weight, (Ib)=58.3% by weight, (Ic)=0.6% by weight, (Id)=0.8% by weight. Purity: 97.9% by weight.

EXAMPLE 8

One may proceed as given in Example 1 but a friction disc stirrer is used and the fourth dilution after the third dilution is carried out after 48 hours. The mixture is stirred for 48 hours at 0° C. and the material is diluted with a further 40 ml (31.5 g) of isopropanol. The mixture is further cooled and at −5° C. it is stirred for 48 hours and at −10° C. for 72 hours. As given in Example 1 90 g of snow white crystalline material are obtained.

M.p.: 62.5° C.

Isomer composition: Ia: 39.0% by weight; Ib: 59.5% by weight; Ic: 0.6% by weight, Id: 0.2% by weight.

EXAMPLE 9

One may proceed as given in Example 1 but 0.1 g DBU is used instead of triethyl-amine. In the first and second combined generation 94 g white crystalline material are obtained.

M.p.: 62.5°–64° C.

Isomer composition: Ia: 39.6% by weight, Ib: 57.2% by weight; Ic: 1.2% by weight; Id: 0.9% by weight.

Purity: 98.9% by weight.

EXAMPLE 10

Seven reactors of capacity 750 ml and equipped with cooler and stirrer are connected to series. The first reactor is cooled to 0° C., the second reactor is cooled to 8° C. and the further reactors are cooled subsequently to 14, 15, 10, 0 and −10° C. Into the reactors 100 g of 1R cis S and 1S cis R (Ia) and 1R trans S and 1S trans R (Ib) isomers are added at a ratio of (Ia):(Ib)=40:60 and at least 95 percent of crystalline 2,2-dimethyl-3-(2′,2-dichlorovinyl)-cyclopropane-carboxylic acid α-cyano-(m-phenoxybenzyl)-ester (Cypermethrin) are added. To the first and second reactor 30 ml isopropanol and 30 ml triethyl-amine are also added and in addition to the third reactor a further 40, and to the fourth reactor 80, to the fifth reactor 120, to the sixth reactor 160 and to the seventh reactor 200 ml of isopropanol are added. The mixtures are thermostated under vigorous stirring. To the first reactor 100 g oily cypermethrin containing all cis and trans isomers at a ratio of 41:59 and of an average purity of 94% and 30 ml of isopropanol are added. The mixtures are continuously stirred and after 12 hours to the first reactor 30 ml of triethyl-amine are charged. The half of the diluted mixture is passed to the next reactor, and the addition of cypermethrin and isopropanol to the first reactor is repeated. After 12 hours the mixture of the first reactor is diluted with 30 ml of triethyl amine and the half of the mixture of the second reactor is passed to the third reactor and half of the content of the first reactor is passed to the second reactor. Then, 100 g of cypermethrin and 30 ml of isopropyl alcohol are again added to the first reactor and after 12 hours stirring the first reactor is diluted with 30 ml of triethyl-amine and the third reactor is diluted with 40 ml isopropanol and the half of the mixtures are passed from the third reactor to the fourth reactor and from the second reactor to the third reactor and from the first reactor to the second reactor.

Repeating the feeding in of cypermethrin and isopropanol after 12 hours stirring and after the passing of the materials the first reactor is diluted with 30 ml triethyl-amine and the 3., 4., 5., 6. and 7. reactors are diluted with 40 ml of isopropanol and the half of the reactors is passed to the next reactor and the product obtained at the end of the reactor chain is passed on the filter and the whole operation sequence is repeated at every 12 hours for any time. The filtered material which contains 0.1% by weight of formaldehyde is washed with isopropanol containing 0.5% acetic acid and dried at room temperature. At each time 85 g of snow white crystalline substance are obtained.

Purity: 97% containing 38.5% of isomer pair Ia and 58.5% isomer pair Ib.

M.p.: 63° C.

Yield: related to the starting material: 85%.

EXAMPLE 11

Seven reactors of capacity of 750 ml equipped with a cooler and stirrer are connected in series. The first reactor is tempered to 20° C., the second reactor to 25° C., the third reactor to 25° C. and the fourth reactor to 20° C. and the further reactors are cooled to temperatures being by 5° C. lower than the previous reactors. To the reactors 100 g isomer pair (Ib) are added containing at least 95% crystalline end-product and to the first and second reactor 30 ml triethylamine and 30 ml isopropanol are given. In addition to that to the third reactor a further 40 and to the fourth reactor 80 and to the fifth reactor 120, to the sixth reactor 180 and to seventh reactor 200 ml isopropanol are given. The mixtures are thermostated under continuous vigorous stirring and then to the first reactor 100 g of oily cypermethrin containing all trans isomers and of an average purity of 94% or cypermethrin melt and 30 ml isopropanol are added. After 12 hours stirring 30 ml triethyl-amine are added to the first reactor. Half of the diluted mixture is passed to the next reactor and the addition of cypermethrin and isopropanol is repeated. After 12 hours the mixture of the first reactor is diluted with 30 ml of triethyl-amine, half of the mixture in the second reactor is passed to the third reactor, and half of the content of the third reactor is passed to the second reactor. Then, 100 g cypermethrin and 30 ml isopropyl-alcohol are again added to the first reactor. After 12 hours stirring the first reactor is diluted with 30 ml of triethyl-amine and the third reactor is diluted with 40 ml of isopropanol. Half of the content of the third reactor is passed to the fourth reactor and from the second reactor to the third reactor and then from the first reactor to the second reactor. By repeating the additions of cypermethrin and isopropanol and after 12 hours stirring the first reactor is diluted with 30 ml triethyl-amine and the 3., 4., 5., 6. and 7. reactors are diluted with 40 ml isopropanol and the half of the content of the reactors is passed to the next reactor and the product obtained at the end of the reactor chain is passed on the filter and the whole operation sequence is repeated at every 12 hours until any time. The filtered material which contains 0.05% by weight of formaldehyde is washed with isopropanol containing 0.5% phthalic acid and dried at room temperature. At each time 85 g of snow white crystalline product are obtained containing 98% of (Ia) isomer pair.

M.p.: 80° C.

EXAMPLE 12

One may proceed as described in Example 10, with the exception that as starting material Cypermethrin containing cis-trans isomers at a ratio of 1:1 is used and as seeding crystal a crystal containing isomers Ia and Ib at a ratio of 1:1 and in an amount of at least 95% is used. 85 g of snow white crystalline substance are obtained.

Purity: 97%.

Isomer ratio Ia and Ib 48:49,

M.p.: 65° C.

EXAMPLE 13

One may proceed as described in Examples 10-13 with the exception that the product obtained at the end of the reactor chain containing 0.2% by weight of formaldehyde is acidified with 2% by weight of aqueous hydrochloric acid solution and extracted under heating to 65° C. with 500 ml heptane and washed hot with 50 ml 1% hydrochloric acid solution, 100 ml of water and 100 ml of saturated sodium-chloride solution and the mixture is crystallized under gradual cooling to −5° C. The precipitated substance is filtered and dried. Every time 87 g of white crystalline product are obtained.

Purity: 98.5%.

Isomer ratio: Ia:Ib=39.0:59.5,

M.p.: 65.5° C.

EXAMPLE 14

One may proceed as given in Example 10 but the product obtained at the end of the reactor chain containing 0.3% by weight of formaldehyde is acidified with 2% by weight of hydrochloric acid. The mixture is extracted with dichloro-ethane, the organic layer is washed with 50 ml of 1% by weight of aqueous hydrochloric acid solution and twice with 100 ml of water, it is evaporated and dissolved in a double amount of methanol and crystallized under gradual cooling to −5° C. Every time 86 g of snow white crystalline product are obtained.

Purity: 98%.

Isomer ratio: Ia:Ib=39:59.

M.p.: 63° C.

EXAMPLE 15

One may proceed as described in Example 10 but the product obtained at the end of the reactor chain is neutralized with 2% by weight of hydrochloric acid, extracted with ethyl-acetate and the organic layer is washed 5 times with 50 ml of 0.5% by weight of aqueous phthalic acid solution containing 0.1% by weight of formaldehyde and after evaporation it is dissolved in a double volume of 2% by weight of phthalic acid-methanol and crystallized under gradual cooling to −5° C. The crystals are filtered and dried. 86 g of snow white crystalline product are obtained.

Purity: 98%,

Isomer ratio: Ia:Ib=39:59;

The isomer ratio was unchanged after a shelf life of 12 months.

M.p.: 63° C.

EXAMPLE 16

One may proceed as disclosed in Example 10 with the exception that after starting the reactor sequence a crystalline cypermethrin of 99.5% purity containing cis and trans isomer at a ratio of 4:6 is used. The material transport is carried out every 24 hours. At the end of the reactor sequence the obtained suspension is acidified with an aqueous solution containing 0.4% by weight of formaldehyde and 2% by weight of hydrochloric acid and it is extracted with 500 ml (433 g) xylene and washed with 50 ml 2% by weight of aqueous phthalic acid solution and 100 ml (1%) maleic acid solution. Thus 535 g Chinmix solution are obtained containing 6.9% isomer pair Ia, 10.6% isomer pair Ib and 0.35% isomer pair Ic and 0.28% isomer pair Id.

EXAMPLE 17

One may proceed as given in Example 10 with the exception that the material obtained at the end of the reactor chain is acidified with an aqueous solution containing 2% by weight of hydrochloric acid and 0.4% by weight of formaldehyde. The mixture is extracted with 400 ml of petrolether (100–120) under heating to 60° C. The organic layer is washed with an aqueous solution containing 0.1% by weight of formaldehyde and 0.1% by weight of hydrochloric acid and the washing is repeated with 50 ml of a solution containing 1% by weight of hydrochloric acid and 0.1% by weight of formaline, with 50 ml water and 50 ml aqueous solution containing 5% by weight of diethyl malonic acid, and the organic layer is separated and the solution is crystallized under slow cooling. After filtration and drying 88 g of snow white crystalline isomer mixture of Ia:Ib=39.0:59.5 is obtained.

Purity: 98%.
M.p.: 65° C.

EXAMPLE 18

One may proceed as given in Example 17 but after washing with malonic acid solution in the last step of the working up for washing 50 ml of water are used and the organic layer is separated. To the solution 0.2 ml of isopropanol is added which contains 0.04 g of maleic acid. The mixture is crystallized under slow cooling. After filtration and drying 87 g of white crystalline product are obtained, which is an isomer mixture of Ia:Ib=39.0:59.5.

Purity: 98.5%,
M.p.: 64°–66° C.

The isomer ratio remained unchanged after a shelf life of 12 months.

EXAMPLE 19

Stability test

A crystalline cypermethrin isomer mixture of 99.9% purity containing in 40% by weight 1 g of isomer pair Ia and in 60% by weight 1 g of isomer pair Ib is dissolved in 2 ml of toluene and the solution is diluted with 8 ml of anhydrous ethanol. Similar solutions are prepared from isomer pairs Ia and Ib, respectively. To the samples various acids as given in the following table are added, dissolved in 10% weight by volume of anhydrous ethanol and 10% by volume of triethyl amine in anhydrous ethanol and the solutions are allowed to stand at room temperature and after 1 week the isomer composition of the substance was examined.

The results are summarized in the following tables.

TABLE I

| Acid | Acid solution, ml | Triethyl-amine solution amount, composition $Y = Ia + Ib$, $X = Ic + Id$ | | | | | | | |
|---|---|---|---|---|---|---|---|---|---|
| | | 0 ml | | 0.01 ml | | 0.1 ml | | 1 ml | |
| | | X (%) | Y (%) | X (%) | Y (%) | X (%) | Y (%) | X (%) | Y (%) |
| — | 0 | 0 | 99.9 | 50 | 49.9 | 47 | 45 | 40 | 43 |
| phthalic acid | 1 | 0 | 99.9 | 0 | 99.9 | 0 | 99.9 | 50 | 49.9 |
| phthalic acid | 2 | 0 | 99.9 | 0 | 99.9 | 0 | 99.9 | 5 | 94.9 |
| Maleinic acid | 1 | 0 | 99.9 | 0 | 99.9 | 0 | 99.9 | 3 | 96.9 |
| Maleinic acid | 2 | 0 | 99.9 | 0 | 99.9 | 0 | 99.9 | 0 | 99.9 |
| Malonic acid | 0.1 | 0 | 99.9 | 0 | 99.9 | 5 | 94.9 | 50 | 49.9 |
| Malonic acid | 1 | 0 | 99.9 | 0 | 99.9 | 0 | 99.9 | 0 | 99.9 |
| Fumaric acid | 1 | 0 | 99.9 | 0 | 99.9 | 0 | 99.9 | 3 | 96.9 |
| Fumaric acid | 2 | 0 | 99.9 | 0 | 99.9 | 0 | 99.9 | 0 | 99.9 |
| Oxalic acid | 1 | 0 | 99.9 | 0 | 99.9 | 0 | 99.9 | 2 | 97.9 |
| Oxalic acid | 2 | 0 | 99.9 | 0 | 99.9 | 0 | 99.9 | 0 | 99.9 |
| para-toluene sulphonic acid | 1 | 0 | 99.9 | 0 | 99.9 | 0 | 99.9 | 49.9 | 50 |
| para-toluene sulphonic acid | 2 | 0 | 99.9 | 0 | 99.9 | 0 | 99.9 | 2 | 97.9 |

TABLE II

| Acid | Acid solution, ml | Triethyl-amine solution amount, composition $Y' = Ib$, $X' = Id$ | | | | | | | |
|---|---|---|---|---|---|---|---|---|---|
| | | 0 ml | | 0.01 ml | | 0.1 ml | | 1 ml | |
| | | X' (%) | Y' (%) | X' (%) | Y' (%) | X' (%) | Y' (%) | X' (%) | Y' (%) |
| — | 0 | 0 | 99.9 | 50.1 | 49.8 | 46 | 45.8 | 41 | 42 |
| phthalic acid | 2 | 0 | 99.9 | 0 | 99.9 | | | 4.9 | 95.1 |
| Maleic acid | 2 | 0 | 99.9 | 0 | 99.9 | 0 | 99.9 | 0 | 99.9 |
| Malonic acid | 1 | 0 | 99.9 | 0 | 99.9 | 0 | 99.9 | 0 | 99.9 |
| Fumaric acid | 2 | 0 | 99.9 | 0 | 99.9 | 0 | 99.9 | 0 | 99.9 |

TABLE III

| Acid | Acid solution, ml | Triethyl-amine solution amount, composition $Y'' = Ia$, $X'' = Ic$ | | | | | | | |
|---|---|---|---|---|---|---|---|---|---|
| | | 0 ml | | 0.01 ml | | 0.1 ml | | 1 ml | |
| | | X'' (%) | Y'' (%) | X'' (%) | Y'' (%) | X'' (%) | Y'' (%) | X'' (%) | Y'' (%) |
| — | 0 | 0 | 99.9 | 50.4 | 49.2 | 48 | 43 | 41 | 42 |
| phthalic acid | 2 | 0 | 99.9 | 0 | 99.9 | 0 | 99.9 | 6 | 94.2 |
| Maleic acid | 2 | 0 | 99.9 | 0 | 99.9 | 0 | 99.9 | 0 | 99.9 |
| Malonic acid | 1 | 0 | 99.9 | 0 | 99.9 | 0 | 99.9 | 0 | 99.9 |
| Fumaric acid | 2 | 0 | 99.9 | 0 | 99.9 | 0 | 99.9 | 0 | 99.9 |
| Oxalic acid | 1 | 0 | 99.9 | 0 | 99.9 | 0 | 99.9 | 2.2 | 97.1 |
| Oxalic acid | 2 | 0 | 99.9 | 0 | 99.9 | 0 | 99.9 | 0 | 99.9 |

EXAMPLE 20

Stability test 1 g of the product of Example 18 is dissolved in 2 ml of toluene and the solution is diluted with 8 ml of anhydrous ethanol and 10% by volume of triethylamine solution is added. The solutions are allowed to stand for 1 week at room temperature and the isomer composition is then examined.

| | X = Ic + Id, Y = Ia + Ib | | | | | |
|---|---|---|---|---|---|---|
| | Amount of triethyl-amine solution (ml) | | | | | |
| Isomer | 0 | 0.01 | 0.02 | 0.05 | 0.1 | 0.2 |
| X (%) | 2 | 2 | 2 | 20 | 48 | 47 |
| Y (%) | 96 | 96 | 96 | 78 | 49.5 | 48 |

EXAMPLE 21

200 g of a reaction mixture containing the crystalline suspension obtained at the end of Example 10 are passed to an apparatus equipped with a heater, stirrer and a discharge at the bottom and it is acidified under steady stirring with an aqueous solution containing 2% by weight of hydrochloric acid and 0.2% by weight of formaldehyde to pH=2. After stirring for 15 minutes the pH of the solution is checked and the crystalline suspension is melted to an emulsion by heating to 60° C. After 15 minutes stirring the oily cypermethrin is sedimented and separated. The warm product is taken up in 150 ml of isopropanol containing 1% by weight of maleic acid and it is crystallized after slow cooling and seeding. The precipitated snow white crystals are filtered, washed with 50 ml of icecold isopropanol containing 1% by weight of maleic acid and dried. Thus 56 g of snow white crystalline product are obtained.

M.p.: 62.5°-63° C.
Purity: 97%.
Isomer ratio: Ia:Ib=38.5-58.5.
Yield related to the starting material: 88%.

EXAMPLE 22

Ona may proceed as given in Example 10, but a thousand times higher size is used and the feeding in and discharging of the materials are performed continuously. The following material flows are ensured:

| order of reactors | material flow in (kg/h) | | | | material flow out (kg/h) |
|---|---|---|---|---|---|
| | cyper-methrin | previous reactor | TEA | IPA | |
| 1 | 8.33 | 0 | 1.83 | 2.0 | 12.16 |
| 2 | 0 | 12.16 | 0 | 0 | 12.16 |
| 3 | 0 | 12.16 | 0 | 2.6 | 14.76 |
| 4 | 0 | 14.76 | 0 | 2.6 | 17.36 |
| 5 | 0 | 17.76 | 0 | 2.6 | 19.96 |
| 6 | 0 | 19.96 | 0 | 2.6 | 22.56 |
| 7 | 0 | 22.56 | 0 | 2.6 | 25.16 |

On a daily average 171.0 kg of a product as given in Example 10 are obtained.

EXAMPLE 23

One may proceed as given in Example 22 but as starting material an oily trans cypermethrin is used and each reactor is filled up with a crystalline material containing 93% of Ib isomers. The mixture is tempered at a temperature given in Example 11, and triethyl amine is led to the second reactor at a flow rate of 1.83 kg/h to increase the crystallizing ability of reactor 1. Thus 173.2 kg of snow-white crystalline product are obtained, which contains isomer pair Ib in 98.1% and melts at 80.5° C.

EXAMPLE 24

To 166.2 g of perlite ($d_{max}=120/\mu m$) 0.8 g of synthetic silicic acid (Aerosil 300) are added in a fluidizing rapid stirrer. 20 g of a cypermethrin mixture of enantiomer-pairs Ia:Ib=4:6 0.04% of fumaric acid and 2 g of fatty alcohol polyglycol ether are added so that the mixture is uniformly homogenized. The powder mixture is ground first in a mechanical mill and afterwards in an air flow mill, whereupon 5 g of octyl phenol polyglycol ether (EO=20) and 2 g of sulfosuccinate are added in a rapid stirrer. The wettable powder mixture (WP) thus obtained is subjected to suspension stability test. Wetting time=23 seconds; floability=89% (standard WHO method).

EXAMPLE 25

5 g of a mixture of cypermethrin enantiomer-pairs Ia:Ib=55:45 and 0.1% of malonic acid are dissolved in a mixture of 21.25 g of xylene and 42.5 g of n-propanol under slow stirring. To the solution a mixture of 4 g of ethoxylated alkyl phenol+calcium salt of linear alkyl aryl sulfonate and a mixture of 6 g of ethoxylated amine-+alkali salt of linear alkyl aryl sulfonate is added under stirring until all the materials are completely dissolved, whereupon 21.25 g of water are added. Thus a transparent solution is obtained which maintains its properties at a temperature between 0° C. and 50° C. for long period of time. The solution can be optionally diluted with water at any rate under the formation of an emulsion having a droplet-size of $0.8–1.5/\mu m$.

EXAMPLE 26

5 g of a mixture of cypermethrin enantiomer-pairs Ia:Ib=25:75 and 0.002 g of diethyl-malonic acid are dissolved in a mixture of 75 g of xylene and 10 g of an aliphatic oil whereupon under slow stirring a mixture (7.5 g) of ethoxylated alkyl phenol+calcium salt of linear alkyl aryl sulfonate and also a mixture (2.5 g) of ethoxylated fatty acid+linear alkyl aryl sulfonate salt are added. When measured according to the method of CIPAC the emulsion concentrate proves to be stable after 170 hours.

EXAMPLE 27

Emulsifiable concentrates (EC) are prepared by admixing the following components:

| 10 EC | |
|---|---|
| Component | Amount, kg/kg |
| Isomer-pairs Ia:Ib = 40:60 | 0.105 |
| diethyl malonic acid | 0.00005 |
| Cyclohexanol | 0.290 |
| Atlox 3386 B | 0.020 |
| Atlox 3400 B | 0.045 |
| Odorless mineral oil | 0.540 |

| 5 EC | |
|---|---|
| Component | Amount, kg/kg |
| Isomer-pairs Ia:Ib = 40:60 | 0.050 |
| Diethyl malonic acid | 0.00005 |
| Cyclohexanol | 0.290 |
| Atlox 3386 B | 0.020 |
| Atlox 3400 B | 0.045 |
| Odorless mineral oil | 0.595 |

EXAMPLE 28

Emulsifiable concentrates (EC) are prepared by admixing the following components:

| 10 EC | |
|---|---|
| Component | Amount, kg/kg |
| Isomer-pair Ib | 0.105 |
| Diethyl malonic acid | 0.00005 |
| Cyclohexanol | 0.290 |
| Atlox 3386 B | 0.020 |
| Atlox 3400 B | 0.045 |
| Odorless mineral oil | 0.540 |

| 5 EC | |
|---|---|
| Component | Amount, kg/kg |
| Isomer-pair Ib | 0.050 |
| Diethyl malonic acid | 0.00005 |
| Cyclohexanol | 0.290 |
| Atlox 3386 B | 0.020 |
| Atlox 3400 B | 0.045 |
| Colorless mineral oil | 0.595 |

EXAMPLE 29

20 g of isomer-pair Ib are diluted with 2 g of ethanol. The solution is admixed in a powder homogenizer with 0.02 g of maleic acid, 5 g of calcium lignosulphonate, 5 g of nonyl-phenyl polyglycol ether (EO=20) and 70 g of calcium carbonate. The product thus obtained is ground in an Alpine 10C type mill. According to CIPAC the floatability amounts to 81%; wetting time=18 seconds.

We claim:

1. A process for the preparation of an isomer mixture of cypermethrin in the form of a stabilized crystalline product of the Formula (I)

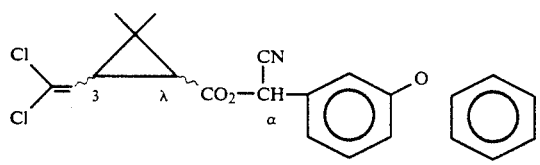

(I)

wherein the carbon atoms indicated by 1, 3 and alpha are chiral carbon atoms and the wavy line indicates cis or trans configuration relative to the cyclopropane ring, said cypermethrin isomer mixture containing out of eight theoretically possible isomers, at least 95% of either the 1RtransS and 1StransR cypermethrin isomer pair (Ib) or an isomer mixture containing only the 1RcisS and 1ScisR cypermethrin isomer pair (Ia) and the cypermethrin isomer pair (Ib) of the ratio (Ia):(Ib) 55:45 to 25:75 from a starting cypermethrin isomer mixture which contains in addition to the cypermethrin isomer pair (Ib), cis and other trans isomers of cypermethrin or the cypermethrin isomer pairs (Ia) and (Ib) in an undesired ratio, which comprises the steps of:

reacting the starting cypermethrin isomer mixture by asymmetrically transforming same in a second order reaction, said starting cypermethrin mixture being an oily or crystalline cypermethrin isomer mixture of at least 90% purity containing at least 60% trans cypermethrin isomers or cis-trans cypermethrin isomers at a ratio of 65:35 to 15:85 in a system containing less than 0.5% of moisture at a temperature of 0° to 25° C. with 0.1 to 0.5 parts by weight of triethylamine or 0.0005 to 0.01 parts by weight of 1,5-diazabicyclo (4, 3, 0) non-5-ene or 1,5-diazabicyclo (5, 4, 0) undecane relative to the weight of the starting cypermethrin isomer mixture under vigorous stirring in propanol or isopropanol to form at first a mixture which is saturated only for desired isomers of the cypermethrin then adding more propanol or isopropanol to maintain the saturation of the desired isomers so that at the end of the reaction a crystalline cypermethrin product, selectively containing cypermethrin isomer pair (Ib) or isomer pairs (Ia) and (Ib) precipitates as a crystalline mass, and the ratio of the propanol or the isopropanol to the cypermethrin isomers forming the crystalline mass is 0.5 to 2 parts by weight of propanol or isopropanol per part of cypermethrin isomers:

then adding an aldehyde as a cyanide binding agent to avoid cyanide emission, and either a) separating the crystalline mass from the reaction mixture, treating the isolated crystalline mass with an acid solution containing 0.1 to 5% by weight of an organic or inorganic acid and optionally dissolving the product in an organic solvent and extracting the solution of the product with an aqueous acid solution containing 0.1 to 5% by weight of acid and isolating the product as a stabilized crystalline cypermethrin or stabilized cypermethrin solution or b) diluting the suspension of the crystalline mass with an aqueous acid solution containing 0.1 to 5% by weight of acid and extracting the base with the aqueous acid in a form of melt or solution in an organic solvent and isolating the product as a stabilized cypermethrin melt or solution;

and optionally recrystallizing the product from a solvent containing 0.1 to 5% by weight of acid to obtain a stabilized crystalline cypermethrin product and isolating same.

2. A process as claimed in claim 1 which comprises cooling the reaction mixture in the last third term of the reaction time gradually below 0° C.

3. A process as claimed in claim 1 for the preparation of an isomer mixture of Ia:Ib=40-60 which comprises using as starting material a mixture of 1RcisS+1ScisR+1RcisR+1ScisS (Ia+Ic)=35-45% by weight, 1RtransS+1StransR+1StransS+1RtransR (Ib+Id)=-50-65% by weight and the ratio of the pyrethroide of the formula (I): triethyl-amine:isopropanol is 1:0.2-0.3-:1-1.5 and continuing the reaction in case of a discontinuous process for 4-10 days at 3°-16° C. and for 1-5 days at 0° C.

4. A process as claimed in claim 1 for the preparation of an isomer mixture of Ia:Ib=50-50% which comprises using as starting material an isomer mixture of (Ia+Ic)=45-55% by weight, (Ib+Id)=45-55% by weight.

5. A process as claimed in claim 1 for the preparation of an isomer mixture of Ia:Ib=25-30:75-70 which comprises using as starting material an isomer mixture of (Ia+Ic)=35-45% by weight, (Ib+Id)=50-55% by weight, and performing the reaction and isolation at 25° C.

6. The process as claimed in claim 1 which comprises using for the extraction of the crystal suspension as a water inmiscible organic solvent.

7. A process as claimed in claim 6 which comprises washing the extract with water, water saturated with sodium chloride or with aqueous mineral or organic acid, optionally containing a cyan binding agent, of a concentration of 0.1–5% by weight.

8. The process as claimed in claim 1 which comprises using formaldehyde as the cyanide binding agent.

9. The process as claimed in claim 1 which comprises using for the recrystallization of the product an apolar or protic solvent mixed with acid.

10. A stabilized arthropodicidal composition which comprises:

(a) as active ingredient, an arthropodicidally effective amount of cypermethrin of the Formula (I)

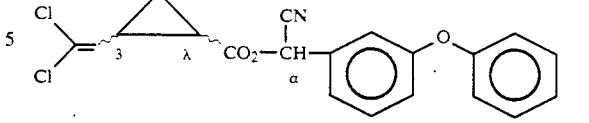

in the form of a stabilized crystalline product wherein the carbon atoms indicated by 1,3 and alpha are chiral carbon atoms, and the wavy line indicates cis or trans configuration relative to the cyclopropane ring, said cypermethrin isomer mixture containing out of eight theroretically possible isomers, at least 95% of either the 1RtransS and 1StransR cypermethrin isomer pair (Ib) or an isomer mixture containing only the 1RcisS and 1ScisR cypermethrin isomer pair (Ia) and the cypermethrin isomer pair (Ib) of the ratio (Ia):(Ib) 55:45 to 25:75; and (b) 0.001 to 0.1% by weight of a stabilizer which is a non-volatile carboxylic acid having a $pK_1$ of 1 to 5 or p-toluene-sulfonic acid.

11. The stabilized arthropodicidal composition defined in claim 10 wherein the non-volatile carboxylic acid having a $pK_1$ of 1 to 5 is phthalic acid, succinic acid, tartaric acid, maleic acid, fumaric acid, malonic acid, diethylmalonic acid or oxalic acid.

* * * * *